(12) United States Patent
Tomita et al.

(10) Patent No.: US 6,683,683 B2
(45) Date of Patent: *Jan. 27, 2004

(54) DEFECT INSPECTION METHOD AND APPARATUS FOR SILICON WAFER

(75) Inventors: Koji Tomita, Hitachinaka (JP); Muneo Maeshima, Mito (JP); Shigeru Matsui, Hitachinaka (JP); Yoshitaka Kodama, Hitachinaka (JP); Hitoshi Komuro, Hitachinaka (JP); Kazuo Takeda, Tokorozawa (JP)

(73) Assignee: Hitachi, Ltd., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 10/084,059

(22) Filed: Feb. 28, 2002

(65) Prior Publication Data

US 2002/0080344 A1 Jun. 27, 2002

Related U.S. Application Data

(63) Continuation of application No. 09/842,929, filed on Apr. 27, 2001, now Pat. No. 6,384,909, which is a continuation of application No. 09/198,093, filed on Nov. 23, 1998, now Pat. No. 6,256,092.

(51) Int. Cl.$^7$ .............................................. G01N 21/88
(52) U.S. Cl. .................................................. 356/237.2
(58) Field of Search ........................ 356/237.1, 237.2, 356/237.3; 250/559.45, 559.46

(56) References Cited

U.S. PATENT DOCUMENTS

| | | | |
|---|---|---|---|
| 5,032,734 A | * 7/1991 | Orazio et al. | 250/559.46 |
| 5,602,401 A | 2/1997 | Broude et al. | 356/237.4 |
| 5,936,726 A | 8/1999 | Takeda et al. | 356/237.2 |
| 6,226,079 B1 | 5/2001 | Takeda et al. | 356/237.2 |
| 6,256,092 B1 | 7/2001 | Tomita et al. | 356/237.1 |
| 6,384,909 B2 | * 5/2002 | Tomita et al. | 356/237.1 |

OTHER PUBLICATIONS

Extended Abstracts of the 1996 International Conference on Solid State Devices and Materials, Aug. 26–29, 1996.
Applied Physics vol. 65, No. 11 (1996), pp. 1162–1163.

* cited by examiner

Primary Examiner—Richard A. Rosenberger
(74) Attorney, Agent, or Firm—Kenyon & Kenyon

(57) ABSTRACT

A defect inspection apparatus for detecting defects existing on a surface of a semiconductor sample and/or inside the sample based on light information from the sample obtained by irradiating a light beam onto the sample is provided, which comprises a detecting means for detecting positions in the depth direction where the defects exist and distribution of the defects based on the light information; a setting means for setting a position in the depth direction where defects exist; and a means for displaying the distribution of the defects obtained by the detecting means, the displaying means displaying the distribution of the defects corresponding to the position in the depth direction set by the setting means.

8 Claims, 6 Drawing Sheets

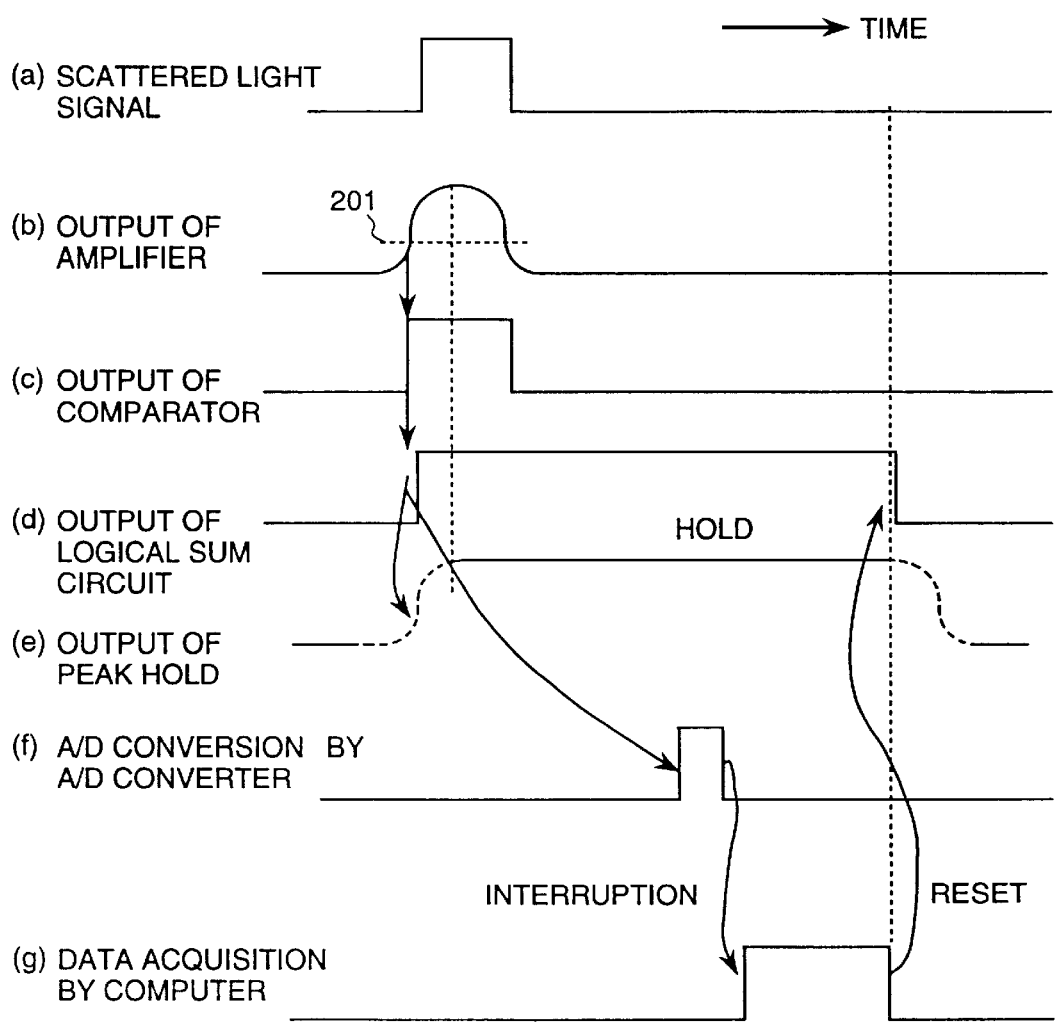

FIG.4A
DEFECT DEPTH  0.5 ~ 5.0  μm
DEFECT PARTICL SIZE  20 ~ 100  nm
[OK]  [CANCEL]
FIG.4B
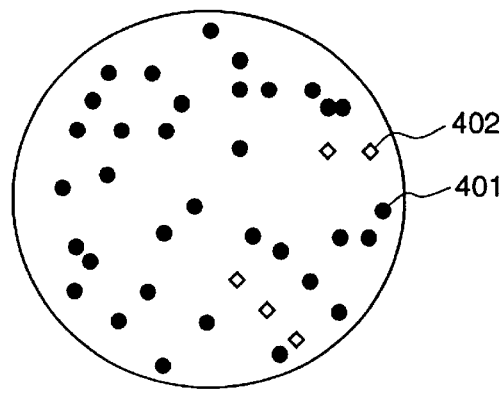
402
401
FIG.4C
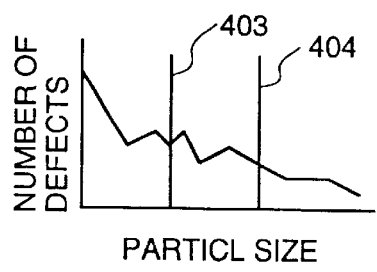
403  404
NUMBER OF DEFECTS
PARTICL SIZE
FIG.4D
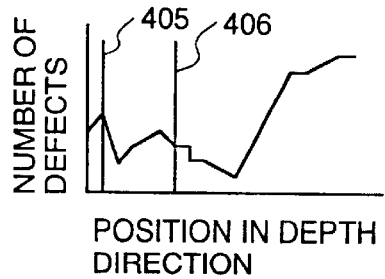
405  406
NUMBER OF DEFECTS
POSITION IN DEPTH DIRECTION

DEFECT INSPECTION METHOD AND APPARATUS FOR SILICON WAFER

This is a continuation of U.S. patent application Ser. No. 09/842,929, filed Apr. 27, 2001 now U.S. Pat. No. 6,384,909, which is a continuation of U.S. patent application Ser. No. 09/198,093, filed Nov. 23, 1998, which issued Jul. 3, 2001 as U.S. Pat. No. 6,256,092.

BACKGROUND OF THE INVENTION

The present invention relates to a defect inspection apparatus and method and, particularly, to an apparatus of measuring a precipitated particle in a semiconductor wafer and a crystal defect, such as a stacking fault, and to a wafer surface extraneous substance inspection apparatus.

As the integration of an LSI (large scale integrated) circuit is being increased, decrease in a conforming item acquisition ratio and decrease in reliability caused by a failed MOS (metal oxide semiconductor) transistor composing the LSI circuit becomes a big problem. As causes of the failed MOS transistor, dielectric breakdown of a gate oxide film and excessive current leak in a junction are typical problems. It is not preferable that a crystal defect is formed in a surface area having elements in a silicon wafer because a failed MOS transistor occurs, as described above.

Therefore, defect measurement is important in the quality control of silicon crystal. In regard to the method measuring such a defect, there is a method in which an infrared ray transmissible through the silicon is irradiated and the scattered light is detected.

Crystal defects exist and are distributed at any positions inside a single crystal. In general, in manufacturing devices such as IC or the like, it is required to develop a wafer which does not have any crystal defect within a range from the crystal surface (mirror surface) to a level of 0.5 $\mu$m depth and contains high density defects in the deep zone.

In developing such a wafer, it is necessary to observe these crystal defects to reflect the observed result to the development. In regard to the observing method, there is described a technology in "Extended Abstracts of the 1996 International Conference on Slid State Devices and Materials, Aug. 26–29, 1996" and "Applied Physics, Vol. 65, No. 11 (1996)", pages 1162–1163.

SUMMARY OF THE INVENTION

In such a prior art, two kinds of light beams, each having a different wavelength which has different characteristics relating to absorption degree of silicon wafer, are irradiated on a silicon wafer, light scattered from a crystal defect inherent in the silicon wafer is detected and is analyzed, thereby the distribution situation of the crystal defect is indicated, or the total number of the crystal defects in a predetermined depth from the surface of the wafer is measured and is indicated.

When the crystal defect inherent in the silicon wafer is observed, and it is analyzed, the distribution situation of these crystal defects and the total number of the crystal defects in every depth from the surface of the wafer are very important factors, and the crystal defect display device for displaying these defects brought results in its own way.

The inventors of the present invention, however, foresaw that it is extremely important that the crystal defect display device display what kind of particle size and how many of the crystal defects are distributed in the respective predetermined depth positions of the silicon wafer.

For example, in the case of hydrogen anneal heat treatment, progress conditions of the heat treatment are distinguished by observing what kind of particle size and how much sludge of $SiO_2$ are distributed in the predetermined depth position of the silicon wafer. By such an observation result, heat treatment conditions, such as temperature and treatment time in the hydrogen anneal heat treatment, can be decided ideally.

Moreover, COPs (Crystal Originated Particles) with many parts which are indistinct in its generating behavior till now are traces of the grown-in defects that remained as pits on the surface of the silicon wafer, and analysis of the most suitable condition of the process that does not produce COPs can be done easily if it can be observed how deep the defects are distributed in the silicon wafer.

In such a prior art, two kinds of light beams having different wave length which has different characteristics relating to absorption degree of silicon wafer are irradiated on a silicon wafer, light scattered from crystal defect to inhere in the silicon wafer is detected and is analyzed, thereby distribution situation of the crystal defect is indicated, or total number of the crystal defect in a predetermined depth from the surface of the wafer is measured and is indicated.

In this way, an object of the present invention is to provide a crystal defect inspection apparatus which makes it possible to observe what kind of particle size and how many of the crystal defects are distributed in various predetermined depths of the silicon wafer.

In order to attain the above objects, the present invention provides a defect inspection apparatus for detecting defects existing on a surface of a sample and/or inside the sample based on light information from the sample obtained by irradiating a light beam onto the sample, which comprises a detecting means for detecting positions in the depth direction where the defects exist and distribution of the defects based on the light information; a setting means for setting a position in the depth direction where defects exist; and a means for displaying the distribution of the defects obtained by the detecting means, the displaying means displaying the distribution of the defects corresponding to the position in the depth direction set by the setting means.

By providing the defect inspection apparatus as described above, defects for which the cause of defect occurrence is different depending on the position in the depth direction, can be selectively displayed by setting a specified position in the depth direction.

BRIEF DESCRIPTION OF THE DRWINGS

FIG. 2 is a chart showing timing acquiring a scattered light signal.

FIGS. 4A, 4B, 4C, 4D are figures showing examples of a selective display of defect distribution.

DETAILED DESCRIPTION

A method of measuring crystal defects and an apparatus for measuring crystal defects in accordance with the present invention will be described below, referring to preferred embodiments.

Figure 1:
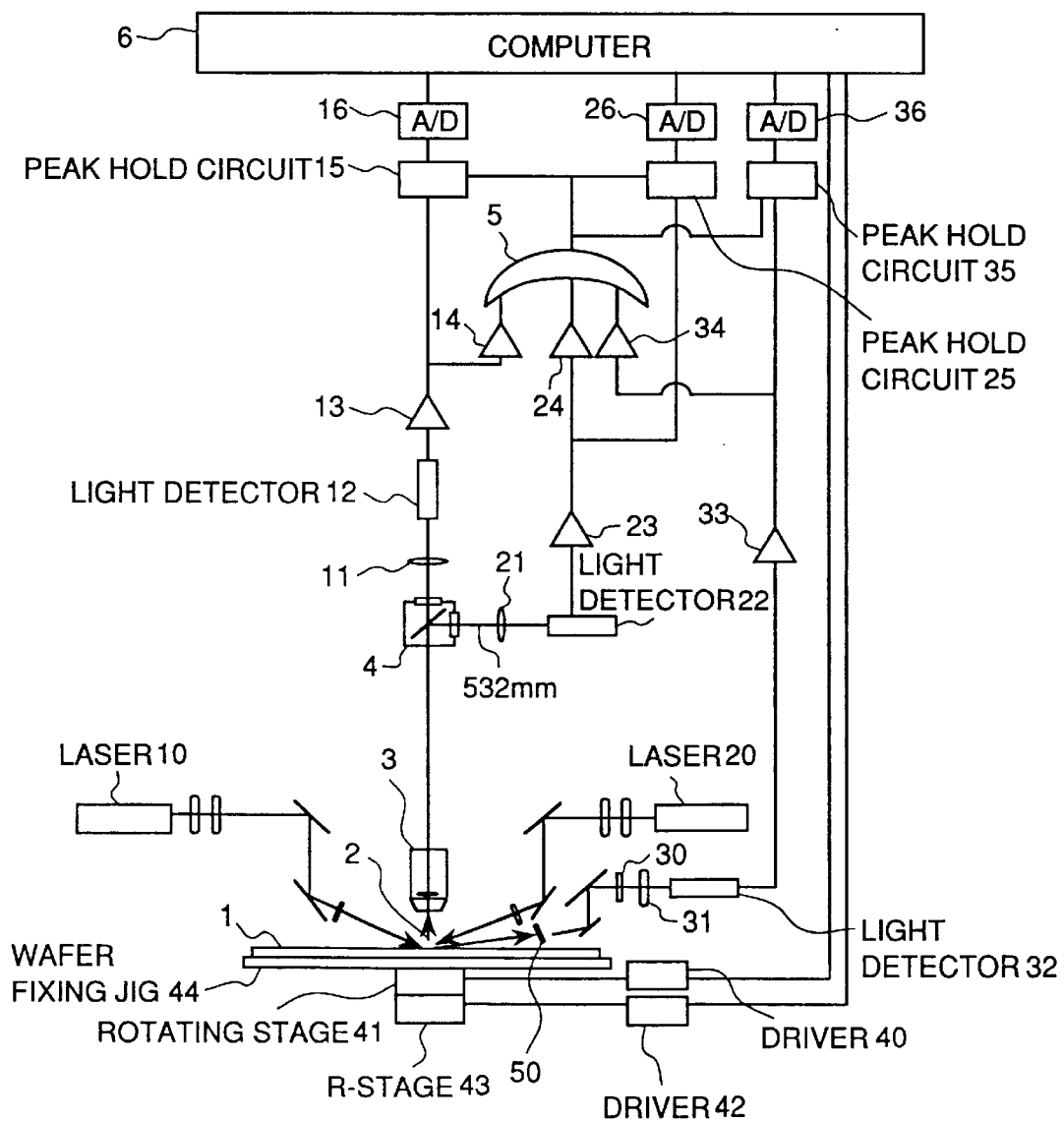
FIG. 1 is a schematic diagram showing the construction of a defect inspection apparatus in accordance with the present invention.

FIG. 1 is a block diagram showing the overall construction of an embodiment of an apparatus for measuring crystal defects in accordance with the present invention. The whole-surface scanning of irradiation light to a silicon wafer is performed in a form of spiral scanning by irradiating a light beam on the silicon wafer which is rotationally being moved and of which the center is linearly being moved. At a moment when a scattering body passes through the irradiating region, a pulse of scattered light is generated. A light beam from a laser 10 of 532 nm wavelength and a light beam from a laser 20 of 810 nm wavelength are irradiated as the irradiating light on a sample wafer 1 fixed onto a wafer fixing jig 44 on a rotating stage 41. Oxygen precipitating particles ($SiO_2$ particles) and crystal defects such as transition contained in the sample wafer 1 and extraneous particles attached onto the wafer surface are detected as scattering bodies by detecting scattered light 2 from each of the defects.

There is provided a system for detecting scattered light scattered in an angle larger than a Brewster angle to the wafer surface. The scattered light scattered in an angle larger than a Brewster angle is concentrated by a lens 50, and selected light of 532 nm wavelength is scattered using a filter 30. Then, the selected light is concentrated to a light detector 32 using a lens 31, and the output signal is amplified by an amplifier 33, and the peak signal intensity held by a peak hold circuit 35 is output and digitized by an A/D converter 36 to be acquired in the computer 6.

The scattered light 2 from the defect is concentrated by an objective lens 3, being branched by a dichroic mirror 4, being separated to a light beam of 810 nm wavelength and a light beam of 532 nm wavelength, being respectively concentrated by lenses 11 and 21, then being respectively detected using light detectors 12 and 22. The detected signals are respectively amplified by amplifiers 13 and 23, and peak signal intensities respectively held by peak hold circuits 15 and 25 are output and digitized by A/D converters 16 and 26 to be acquired in a computer 6.

There is provided a system for detecting scatted light scattered in an angle larger than Brewster angle to the wafer surface. The scatted light scattered in an angle larger than Brewster angle is concentrated by a lens 50, and select scattered light of 532 nm wavelength using a filter 30. Then, the selected light is concentrated to a light detector 32 using a lens 31, and the output signal is amplified by an amplifier 33, and the peak signal intensity held by a peak hold circuit 35 is output and digitized by an A/D converter 36 to be acquired in the computer 6.

On the other hand, scattered light measurement is performed while the rotating stage 41 and an R-stage 43 are scanned in a rotating direction (θ direction) and a radial direction (R direction) using drivers 40, 42 by the computer 6 and while coordinates (R, θ) of a rotation encoder and a linear encoder attached to the wafer fixing jig 44 are being monitored. Coordinates (R, θ) at an instant when scattered light from a defect occurs is acquired together with the scattered light intensity signal to the computer 6.

A display (not shown in the figure) is connected to the computer 6 to display defect information to be described later.

Data acquisition timing at occurrence of scattered light from the defect will be described below, referring to the scattered light signal acquisition timing chart shown in FIG. 2. As shown in FIG. 2 (a), a light beam having 532 nm wavelength and a light beam having 810 nm wavelength are irradiated on and scattered by a defect. The scattered light is acquired by each of the detectors. Taking the light beam having 532 nm wavelength, when an output signal of the amplifier 13 exceeds a preset threshold value 201 as shown in FIG. 2 (b), an output signal, shown in FIG. 2 (c), from a comparator 14 gives a trigger output to the peak hold circuit 15 through a logical sum circuit 5 shown in FIG. 2 (d), and the peak hold circuit 15 holds a peak intensity of the amplifier 13 as shown in FIG. 2 (e). In regard to a scattered light signal of the light having 810 nm wavelength or a scattered light intensity signal, a peak intensity is held in the peak hold circuit 25 or 35 similarly to the case of the scattered light signal of the light having 532 nm wavelength.

The peak intensity values are respectively digitized by the A/D converters 16, 26, 36 at a certain time after the trigger output from the logical sum circuit 5 as shown in FIG. 2 (f), and acquired to the computer 6 and stored in a memory after completion of the A/D conversion as shown in FIG. 2 (g). At that time, the computer 6 also stores the coordinates (R, θ) of the rotation encoder and the linear encoder at a time as a position at the wafer surface position of which the scattered light occurs. After the data is acquired in the computer 6, the output of the logical sum circuit and the peak hold are reset. In this embodiment, the coordinates are stored together with a kind of the unit region to which the coordinates belong.

Figure 3A:
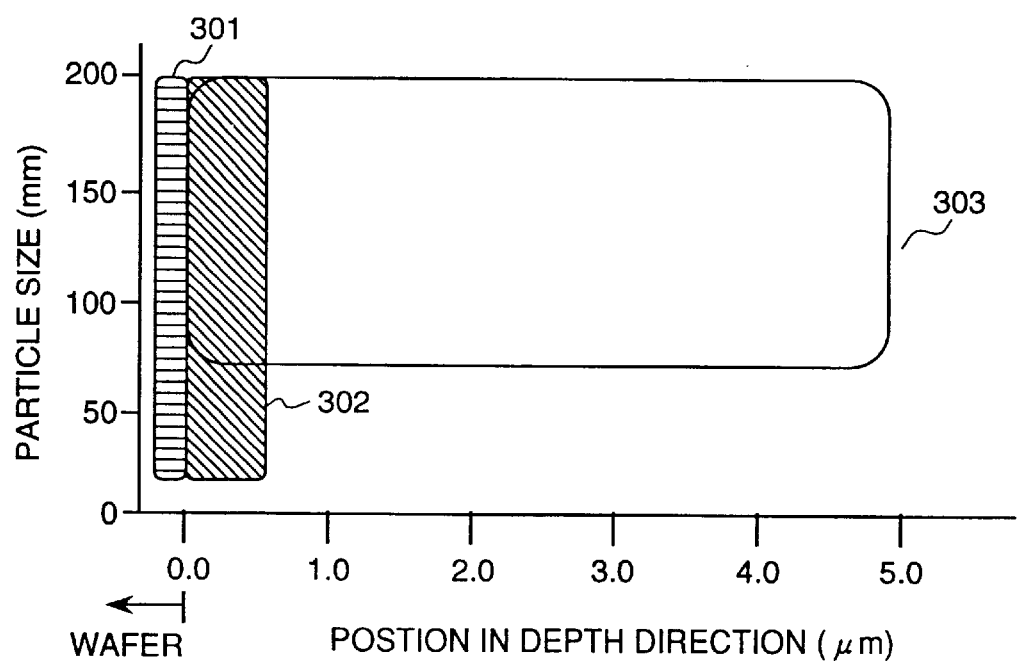
FIGS. 3A, 3B, 3C are relational diagrams showing detectable range by the scattered light signal.
Figure 3B:
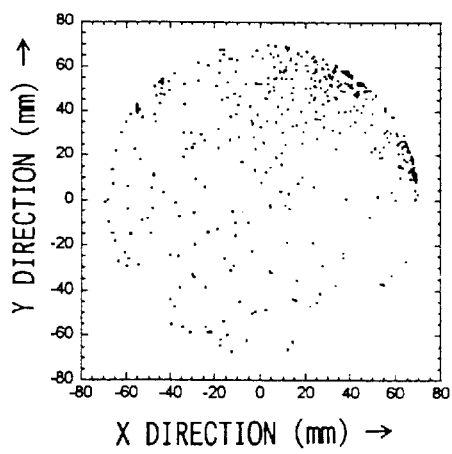
Figure 3C:
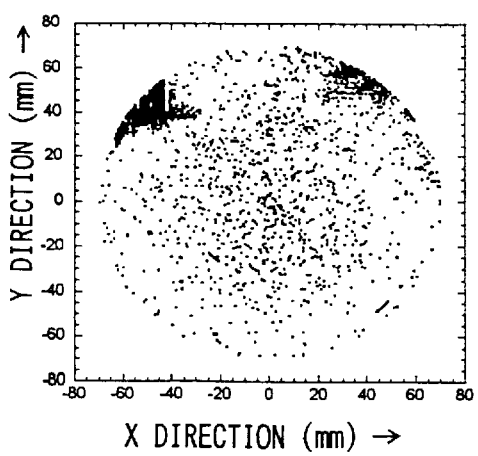

FIG. 3A is a graph showing the relationship between position in the depth direction where a defect is detectable and dimension of the defect when each of the scattered light intensity signals exceeds each of the threshold values of the detectors. When any one of the scattered light intensity signal (the signal of the light detector 12) of 532 nm wavelength, the scattered light intensity signal (the signal of the light detector 22) of 810 nm wavelength and the scattered light intensity signal by the light detector 32 exceeds a certain threshold value, as described above, by acquiring the scattered light intensity and the coordinates of the wafer surface at that time it is possible to detect the defects in all the ranges of the defect detection range 301 by the trigger of the detector for detecting surface extraneous particles, the defect detection range 302 by the trigger of the detector for scattered light of 532 nm wavelength and the defect detection range 303 by the trigger of the detector for scattered light of 810 nm wavelength. Thereby, for example, in an epitaxial wafer which will be widely used, it is possible to detect defects an epitaxial layer including a substrate under the epitaxial layer other than defects in the epitaxial layer of nearly 1 μm thickness by a single measurement of whole wafer surface scanning. Since characteristic of defects in the epitaxial layer is different from characteristic of defects in the substrate under the epitaxial layer, the capability of detecting the defects in both of the zones together can provide useful information for analyzing cause of failure in a wafer manufacturing process. For example, defects in the epitaxial layer can be found by the defect detection by the trigger of the scattered light detector of 532 nm wavelength, as shown in FIG. 3B, but defects in a deeper position cannot be detected even if they exist. In the defect detection by the trigger of the scattered light detector of 810 nm wavelength, defects called as slippage existing in a deeper portion up to 5 μm could be detected, as shown in FIG. 3C. The slippage is a defect which is generated in an edge portion of a wafer caused by temperature difference between the central portion and the peripheral portion when the wafer is heat treated, and it is a serious problem when the wafer has a large diameter. From the slippage generated in the peripheral portion of the wafer in this embodiment, it is possible to obtain information that there is a problem in the work for inserting the wafer into a heat treatment furnace.

In the irradiation feature described above, the measurement may be performed by displacing the irradiating position of the light beam of 532 nm wavelength so that the light beam of 532 nm wavelength is irradiated earlier than the light beam of 810 nm wavelength in time as the light beams are scanned. The system is designed so that only the signal of 810 nm wavelength is acquired when the scattered light intensity signal (the signal of the light detector 12) of 532 nm wavelength does not exceed the threshold value and the scattered light intensity signal (the signal of the light detector 22) of 810 nm wavelength exceeds a certain threshold value. In this case, since defects of which the position in the depth direction can be determined are within the penetrable depth of the light beam of 532 nm wavelength, it is unnecessary to derive positions in the depth direction for the data that the scattered light intensity signal (the signal of the light detector 12) of 532 nm wavelength has a value smaller than the certain threshold value.

The position in the depth direction and the dimension (particle size) of defect of the embodiment in accordance with the present invention are calculated as follows.

The calculation procedure for obtaining the defect position in the depth direction will be described below. Letting a refractive index of a substance for wavelength $\lambda$ be n and an attenuation coefficient be k, the penetrable depth $\Gamma$ where an amplitude of the incident light becomes 1/e of a value just below the surface of the substance can be expressed by Equation 1.

$$\Gamma = \lambda / 2\pi k \quad (1)$$

Therefore, an intensity at a depth z from the surface of light incident to the substance from air atmosphere with an incident angle $\theta$ is attenuated from the intensity at just below the surface by $\exp((-2z/\Gamma)\cos(\arcsin(\sin\theta/n)))$. Therefore, when the light beam is irradiated from air atmosphere onto the substance at the incident angle $\theta$, an intensity of scattered light from a defect which exists at a position of a depth Z from the surface of the substance can be expressed by Equation 2. Therein, $\sigma$ is an integrated scattering cross section when scattered light toward the sample surface is detected with a certain solid angle, and I is an intensity of the incident light beam.

$$S = I\sigma \exp[-(2z/\Gamma)(1+1/\{\cos(\arcsin(\sin\theta/n))\})] \times Ti \times Tf \quad (2)$$

where Ti is a transmissivity of the incident light beam from the air atmosphere to a position just below the surface of the substance, and Tf is a transmissivity of the scattered light from a position just below the surface of the substance to the air atmosphere.

Letting refractive indexes of a substance for wavelengths $\lambda 1, \lambda 2$ be n1, n2, penetrable depths be $\Gamma 1, \Gamma 2$, intensities of incident light beams be I1, I2, intensities of measured scattered light be S1, S2, integrated scattering cross sections be $\sigma 1, \sigma 2$, transmissivities of the incident light beam from the air atmosphere to a position just below the surface of the substance be T1i, T2I, and transmissivities of the scattered light from a position just below the surface of the substance to the air atmosphere be T1f, T2f, respectively, Equation 3 and Equation 4 are stisfied.

$$S1 = I1 \cdot \sigma 1 \exp[-(2z/\Gamma 1)(1+1/\{\cos(\arcsin(\sin\theta/n1))\})] \times T1i \times T1f \quad (3)$$

$$S1 = I2 \cdot \sigma 2 \exp[-(2z/\Gamma 2)(1+1/\{\cos(\arcsin(\sin\theta/n2))\})] \times T2i \times T2f \quad (4)$$

From the above equations, the position z of the defect in the depth direction can be expressed by Equation 5 to Equation 7.

$$z = C1 \cdot \ln[C2(S1/S2)(\sigma 2/\sigma 1)] \quad (5)$$

$$C1 = 1/[(4\pi k2/\lambda 2)(1+1/\{\cos(\arcsin(\sin\theta/n2))\}) - (4\lambda k1/\lambda 1)(1+1/\{\cos(\arcsin(\sin\theta/n1))\})] \quad (6)$$

$$C2 = I2/I1 \times T2i \times T2f/(T1i \times T1f) \quad (7)$$

In order to obtain the position of the defect in the depth direction in the present invention, it is necessary to calculate a dimension of the defect in advance. If a light beam of a wavelength $\lambda 1$ capable of penetrating the sample, that is, a light beam of a wavelength $\lambda 1$ having a sufficiently large $\Gamma 1$ ($\Gamma 1 >> \Gamma 2$) is used in Equation 3, an integrated scattering cross section $\sigma 1$ in a certain detecting solid angle can be expressed by Equation 8.

$$\sigma 1 = S1/(I1 \times T1i \times T1f) \quad (8)$$

Since the values T1i, T1f can be calculated from the optical principle, the value of the integrated scattering cross section $\sigma 1$ can be calculated by measuring S1 if the value I1 is measured in advance. Therefore, when a refractive index of the defect is known, a dimension of the defect can be calculated from conventional Mie's scattering theoretical equation.

Since a value of the integrated scattering cross section $\sigma 2$ in a certain detecting solid angle by light having a wavelength $\lambda 2$ absorbed in the sample can be calculated when the dimension of the defect is known, a ratio $\sigma 1/\sigma 2$ of the integrated scattering cross sections can be determined. Similarly to the above, the values T2i, T2f are calculated from the optical principle, the value C2 can be calculated from Equation 7 by measuring the value I2 in advance. The value C1 can be also calculated by Equation 1 using a material constant and an experimental condition. By substituting these values into Equation 5, the position z in the depth direction can be obtained.

The dimension (particle size) of a defect may be also obtained by Rayleigh scattering.

The position of a defect in the depth direction and the dimension of the defect obtained as described above are used in order to perform the following display based on the scattered light intensity signals, the coordinates and the kind of unit region to which the coordinates belong described previously.

FIG. 4 shows an example of a selective display of defect distribution in accordance with the present invention. There is provided a means for specifying a range of positions of defects in the depth direction and a range of particle size on polyester basis as the dimension of defects by inputting numerals, as shown in FIG. 4 (a), and the defects within the specified ranges are displayed as planar distributions of defects inside the surface layer 410 and extraneous particles on the surface 402 as shown in FIG. 4 (b).

Since a range of a specific problem zone affecting device forming or a range of defect dimension can be arbitrarily specified by direct inputting after whole surface scanning measurement of a wafer as described above, it is possible to arbitrarily and selectively display a distribution of crystal defects existing inside the surface layer near the surface or a distribution of surface extraneous particles.

A particle size and an existing depth of a defect (including a flaw) formed in a wafer may be different depending on which process out of the manufacturing processes the defect is produced in. That is, if a particle size and an existing depth of a defect can be checked, it is possible to specify which process out of the manufacturing processes the defect is produced in.

Therefore, if a specified particle size, a specific depth or the both can be selectively set and the defects fit to the setting can be selectively displayed, it is easy to observe the features of which process defects are produced in and what number of defects are produced.

In the example of planar distribution disclosed in "Applied Physics, Vol. 65, No. 11 (1996)", pages 1162–1163 described in the article "Background of the Invention", it is difficult to selectively check defects having specific information because all the defects are displayed.

In this embodiment in accordance with the present invention, since a defect existing depth and/or a dimension (particle size) of defects can be set and distribution of the defects of a wafer can be displayed based on the setting, it is possible to understand a process in which the defects are produced and the feature of the produced defects from the defect existing depth and the dimension of the defects. An embodied example will be described below in detail.

A semiconductor wafer (silicon wafer) is manufactured by slicing a single crystal ingot obtained through a single crystal manufacturing method such as CZ method, FZ method or the like into a disk, then by lapping and etching the sliced disk in shaving processes, and finally cleaning the disk after polishing. In a case of an epitaxial wafer, an epitaxial layer is vapor grown after that, and treatment such as polishing is performed again. There may be other processes depending on kind of the wafer.

Defects (flaws) in connection with polishing among the above-mentioned processes are apt to be formed on the wafer surface over a wide range of particle sizes. Defects (COP) which have large particle sizes and appear on the surface are apt to be increased in number by performing heat treatment in a single crystal manufacturing process. In the cleaning process, defects appearing on the wafer surface are apt to be increased in number.

Further, crystal defects formed inside the wafer are produced, for example, in the growing process of epitaxial layer, and particularly, oxygen precipitation particles ($SiO_2$) among the crystal defects are apt to be increased in number toward the depth direction of the wafer.

There are the defect characteristics depending on the manufacturing processes as described above. Therefore, by displaying the defects specific to each of the manufacturing processes distinguishing from the other defects, a trend of the defects produced in each of the processes can be specified.

For example, by setting a position in the depth direction, it is possible to judge whether or not the defects are crystal defects existing inside the wafer or whether or not the defects are defects produced by polishing or cleaning. Further, by a wafer image not containing these kinds of defects, it is possible to easily judge a trend and a degree of defects produced a specific cause of defect occurrence.

The maximum particle size of defects existing in each position in the depth direction is proportionally displayed by the diameter of the cylinder. Further, surface extraneous particles are expressed by a cube. By doing so, the feature of distribution of defect regions on the wafer surface and inside the surface layer can be identified at a glance, and accordingly a problem region can be specified speedily.

It becomes easy to distinguish between surface working failure and inner crystal failure, for example, to judge whether or not the defects are uniformly distributed independently of the depth, whether or not most of the defects are distributed in the deep zones. Further, it is also possible to judge at a glance that the defects are surface extraneous particles or crystal defects.

Further, it is also possible that number of defects for each particle sizes and number of defects for each of positions in the depth direction are displayed in the form of histogram as shown in FIG. 4 (c), and a planar distribution as shown in FIG. 4 (b) is displayed using a pointing device such as a mouse on the graphs to specify a minimum particle size by a trace cursor 403, a maximum particle size by a trace cursor 404, a position of the minimum depth by a trace cursor 405 and a position in the maximum depth by a trace cursor 406. By doing so, it is possible to visually select a range of a specific problem region where number of defects is actually large, to display by selectively setting a particle size or a depth of which number of defects are large, and to selectively display a distribution of crystal defects existing near the surface or a distribution of surface extraneous particles in a region where some problem is considered to actually exist.

Although defects existing in a set depth are displayed distinguishing from the other defects in this embodiment, it is possible, for example, that only the defects existing in the set depth are displayed.

Figure 5:
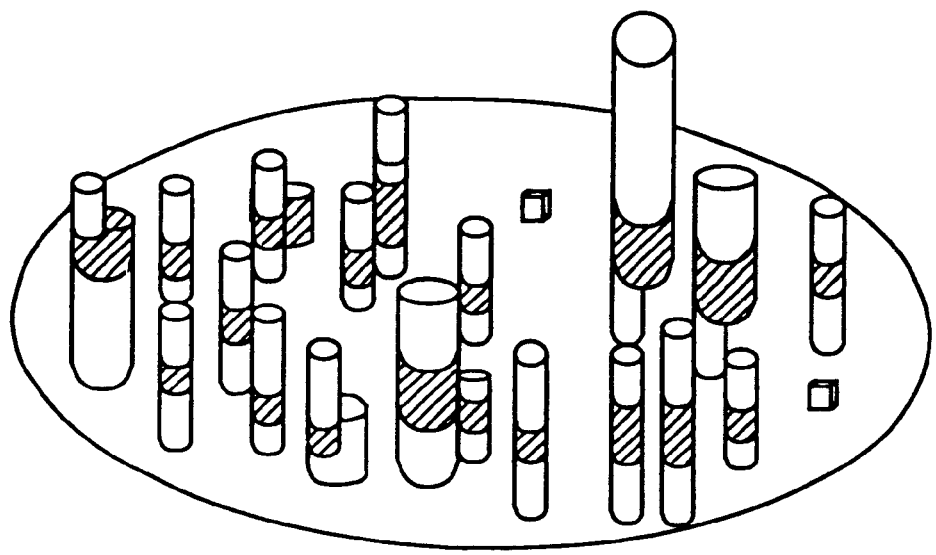
FIG. 5 is a view showing an example of an at-a-glance display of defect distribution.
Figure 6:
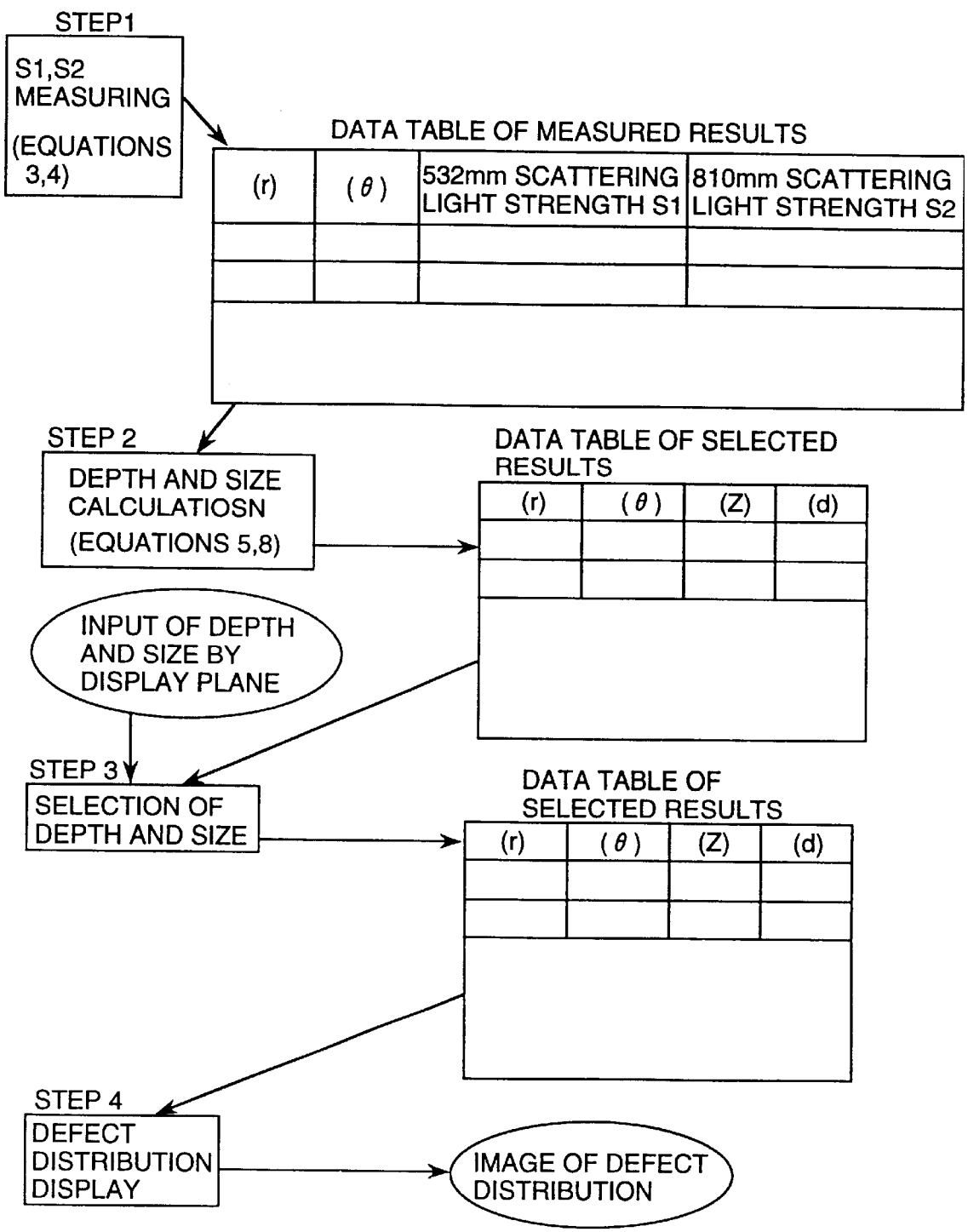
FIG. 6 shows a flowchart for being performed in the computer 6 and for outputting the defect information obtained by setting the depth of the defects.

FIG. 5 is a view showing an example of an at-a-glance display of defect distribution in accordance with the present invention. In this embodiment, defects existing in each of divided unit regions are three-dimensionally displayed on a display simulating a wafer by a cylindrical shape for each unit region, and number of the defects is expressed by the height of the cylinder and a position of the defect existence is expressed by coloring.

The display for each of the unit regions is useful to specify the trend of defect occurrence compared to a simple defect distribution diagram.

The maximum particle size of defects existing each position in the depth direction is proportionally displayed by the diameter of the cylinder. Further, surface extraneous particles are expressed by a cube. By doing so, the feature of distribution of defect regions on the wafer surface and inside the surface layer can be identified at a glance, and accordingly a problem region can be specified speedy.

It becomes easy to distinguish between surface working failure and inner crystal failure, for example, to judge whether or not the detects uniformly distribute independently of the depth, whether or not most of the defects distribute near the surface layer, or whether or not most of the defects distribute in the deep zones. Further, it is also possible to judge at a glance that the defects are surface extraneous particles or crystal defects.

According to the above-mentioned display, the cylindrical rod graph is employed so as to easily understand the number of defects, a depth and a maximum particle size in each of the unit regions. With a rod graph of this type, it is easy to understand the relationship among plural kinds of information. Further, information on the number of defects or maximum particle size differs depending on the depth, the difference can be visually and easily judged by the display shown in FIG. 5.

In the apparatus of this embodiment, positions in the depth direction, dimensions and number of defects are detected. Therefore, defect analysis can be easily performed by judging a trend of defect occurrence based on the plural kinds of information.

As described above, according to the present invention, since defect distribution is displayed based on setting of a specified particle size, a specific depth or the both, it is possible to specify the feature of produced defects and it is easy to specify in which process defects are produced and what kind of defects are produced.

Further, since the defect information for each of the unit regions is displayed, it is easy to specify the trend of defect occurrence.

Thereby, it becomes easy to analyze the defects, and it is possible to provide a defect inspection apparatus suitable for performing the quality control of products and for specifying the cause of occurrence of defects.

According to the calculation stated above performed by the computer 6, a flowchart for outputting the defect information obtained corresponding to the location of the wafer surface by setting the depth of the difects will be explained.

That is, according to step 1 based on equations 3, 4, strengths S1, S2 of the scattering light beams are detected on coordinate positions radius (R), direction (θ) of the stage top where the wafer is mounted and a data table thereof is formed. In step 2, depth (Z) of the defect and particle size (d) are calculated based on these detected scattering light strength S1, S2 according to equations 5, 8, and a data table of the depth (Z) and the particle size (d) is formed corresponding to the coordinate position of the radius (R) and the direction (θ)

In step 3, using a display screen which shown in FIG. 4 (*a*), the depth (Z) and the particle size (d) of the defect are input to be selected, and a data table as a selected result is provided.

When indication of the distribution of the defects is ordered in step 4, the defects in the depth (z) and the particle size (d) of the selected defects are indicated on the stage of the radius (r) and the direction (θ) and a display screen of the defect distribution is provided as shown in FIG. 4 (*b*).

What is claimed:

1. Defect inspection equipment for inspecting defects inherent in a wafer by scanning the wafer with a light beam and detecting light scattered from the defects, comprising:

a light source for generating at least two light beams having wavelengths different from each other, a detecting device for detecting light information scattered from said defects by scanning said wafer with said beams from said light source and outputting scattered light intensity signals at each of said wavelength, a setting means for setting up depth information and particle size information of said defects, an output means for outputting information about said defects at each scan position on said wafer from said light information corresponding to said information set by said setting mean and detected when any one of the scattered light intensity signals exceeds a certain threshold value of the detector, and a display for indicating said information about said defects output from said output means corresponding to each of said scan positions.

2. Defect inspection equipment for inspecting defects inherent in a wafer as defined in claim 1, wherein said information about said defects relates to said particles size information about said defect.

3. Defect inspection equipment for inspecting defects inherent in a wafer as defined in claim 2, wherein said display displays said particle size of said defects corresponding to said information set up on said setting means.

4. Defect inspection equipment for inspecting defects inherent in a wafer as defined in claim 1, wherein said information about said defects relates to number of said defects at each scan position of said wafer.

5. Defect inspection equipment for inspecting defects inherent in a wafer as defined in claim 4, wherein said display displays a number of said defects at each scan position on said wafer corresponding to said at least one information set up on said setting means.

6. Defect inspection equipment for inspecting defects inherent in a wafer as defined in claim 4, wherein said display displays distribution of said defects corresponding to said at least one information set up on said setting means and corresponding to position of said defects on said wafer.

7. Defect inspection equipment for inspecting defects inherent in a wafer as defined in claim 1, wherein said display displays said particle size and number of said defects corresponding to said at least one information set up on said setting means and corresponding to positions of said defects on said wafer.

8. Defect inspection equipment for inspecting defects inherent in a wafer as defined in claim 1, wherein said display displays distribution of said defects corresponding to said at least one information set up on said setting means and corresponding to positions of said defects on said wafer.

* * * * *

UNITED STATES PATENT AND TRADEMARK OFFICE
CERTIFICATE OF CORRECTION

PATENT NO. : 6,683,683 B2
DATED : January 27, 2004
INVENTOR(S) : Koji Tomita et al.

It is certified that error appears in the above-identified patent and that said Letters Patent is hereby corrected as shown below:

Column 3,
Lines 40 and 42, change "scatted light" to -- scattered light --.
Line 41, before "brewster" insert -- a --.
Line 43, change "select" to -- selected --.
Line 44, change "wavelength using" to -- wavelength is scattered using --.

Column 8,
Line 36, change "speedy" to -- speedily --.
Line 39, change "detects uniformly distribute" to -- defects are uniformly distributed --.
Line 41, change "distribute" to -- are distributed --.

Signed and Sealed this

Twenty-first Day of June, 2005

JON W. DUDAS
*Director of the United States Patent and Trademark Office*